US009835608B2

(12) United States Patent
Amanullah et al.

(10) Patent No.: US 9,835,608 B2
(45) Date of Patent: Dec. 5, 2017

(54) METHOD FOR ASSESSING ABLATION MODULAI OF MUDCAKES TO PREDICT EASE OF MUDCAKE REMOVAL OR CLEANING EFFICIENCY OF CLEANING/WASHING/SPACER FLUIDS

(71) Applicant: Saudi Arabian Oil Company, Dhahran (SA)

(72) Inventors: Md. Amanullah, Dhahran (SA); Mohammed Al-Arfaj, Dhahran (SA); Adel Al-Ansari, Dhahran (SA)

(73) Assignee: SAUDI ARABIAN OIL COMPANY (SA)

(*) Notice: Subject to any disclaimer, the term of this patent is extended or adjusted under 35 U.S.C. 154(b) by 445 days.

(21) Appl. No.: 14/109,275

(22) Filed: Dec. 17, 2013

(65) Prior Publication Data
US 2014/0174168 A1 Jun. 26, 2014

Related U.S. Application Data

(60) Provisional application No. 61/739,828, filed on Dec. 20, 2012.

(51) Int. Cl.
*G01N 33/28* (2006.01)
(52) U.S. Cl.
CPC .................. *G01N 33/2823* (2013.01)
(58) Field of Classification Search
CPC .... G01N 15/06; G01N 33/2823; G01N 15/04; G01N 11/14; G01N 33/18; G01N 33/32; G01N 33/343; E21B 21/08; E21B 49/005
(Continued)

(56) References Cited

U.S. PATENT DOCUMENTS 2,830,266 A 4/1958 Southwick et al.
4,430,889 A 2/1984 Sutton
(Continued)

FOREIGN PATENT DOCUMENTS

WO 2010/0017899 A2 2/2010

OTHER PUBLICATIONS

PCT International Search Report and the written opinion dated Mar. 27, 2014; International Application No. PCT/US2013/075663; International filing date Dec. 17, 2013.
(Continued)

*Primary Examiner* — John Fitzgerald
(74) *Attorney, Agent, or Firm* — Bracewell LLP; Constance Gall Rhebergen; Brad Y. Chin

(57) ABSTRACT

Disclosed is a method and apparatus for determining an ablation modulus of a mudcake on a wellbore wall. According to various embodiments of the invention, the method includes preparing a mudcake, forming a mudcake assemblage comprising the prepared mudcake, screen, and a filter paper, and submerging and securing the mudcake assemblage in a container filled with a fluid. The fluid includes one of a native fluid and a foreign fluid to the mudcake. The method further includes agitating the fluid for a plurality of time intervals, removing the mudcake assemblage from the container after expiration of each time interval, and drying the mudcake assemblage. Further, the method includes weighing the mudcake assemblage to determine an interval weight for each time interval, and determining the ablation modulus of the mudcake on the wellbore wall by graphically correlating the determined interval weights of the remaining mudcake in the mudcake assemblage as a function of time. The ablation modulus of the mudcake is defined by a slope of a tangent of an initial portion of the graphical correlation
(Continued)

between the determine interval weights and cumulative time.

17 Claims, 5 Drawing Sheets

(58) Field of Classification Search
USPC ............ 73/53.01, 53.05, 61.62, 151, 152.01,
73/152.07, 152.21, 152.22, 152.61, 865.6;
166/250.01; 175/40
See application file for complete search history.

(56) References Cited

U.S. PATENT DOCUMENTS

| | | | |
|---|---|---|---|
| 4,528,842 A | 7/1985 | Brown | |
| 5,309,761 A * | 5/1994 | Ravi | E21B 49/005 73/152.21 |
| 5,361,631 A | 11/1994 | Covington et al. | |
| 5,874,386 A * | 2/1999 | Chan | C09K 8/524 166/297 |
| 6,055,874 A | 5/2000 | Onan et al. | |
| 6,260,409 B1 | 7/2001 | Briaud et al. | |
| 6,269,684 B1 | 8/2001 | Maki, Jr. et al. | |
| 6,394,185 B1 | 5/2002 | Constien | |
| 6,543,276 B2 | 4/2003 | Murphy, Jr. et al. | |
| 6,619,394 B2 | 9/2003 | Soliman et al. | |
| 6,686,323 B2 | 2/2004 | Nilsson et al. | |
| 6,817,414 B2 | 11/2004 | Lee | |
| 7,647,821 B2 | 1/2010 | Bloomquist et al. | |
| 2004/0238218 A1* | 12/2004 | Runia | E21B 10/60 175/57 |
| 2007/0261855 A1 | 11/2007 | Brunet et al. | |
| 2009/0000361 A1 | 1/2009 | Bloomquist et al. | |
| 2011/0214874 A1 | 9/2011 | Dakin et al. | |
| 2011/0278004 A1 | 11/2011 | Ali et al. | |
| 2012/0108471 A1* | 5/2012 | Amanullah | C09K 8/08 507/104 |
| 2012/0181019 A1* | 7/2012 | Saini | B82Y 30/00 166/250.01 |

OTHER PUBLICATIONS

Md Amanullah, "A Novel Laboratory Method for Assessing the Erosional Characteristics of Mudcakes", SPE, CSIRO Petroleum, May 2006, p. 245-251, SPE Production & Operations.

Md Amanullah, "A Novel Method of Assessment of Spurt and Filtrate Related Formation Damage Potential of Drilling and Drilling-in Fluids", SPE, CSIRO Petroleum, SPE Asia Pacific Oil and GFas Conference and Exhibition, Apr. 15-17, 2003, pp. 1-9, Society of Petroleum Engineers.

* cited by examiner

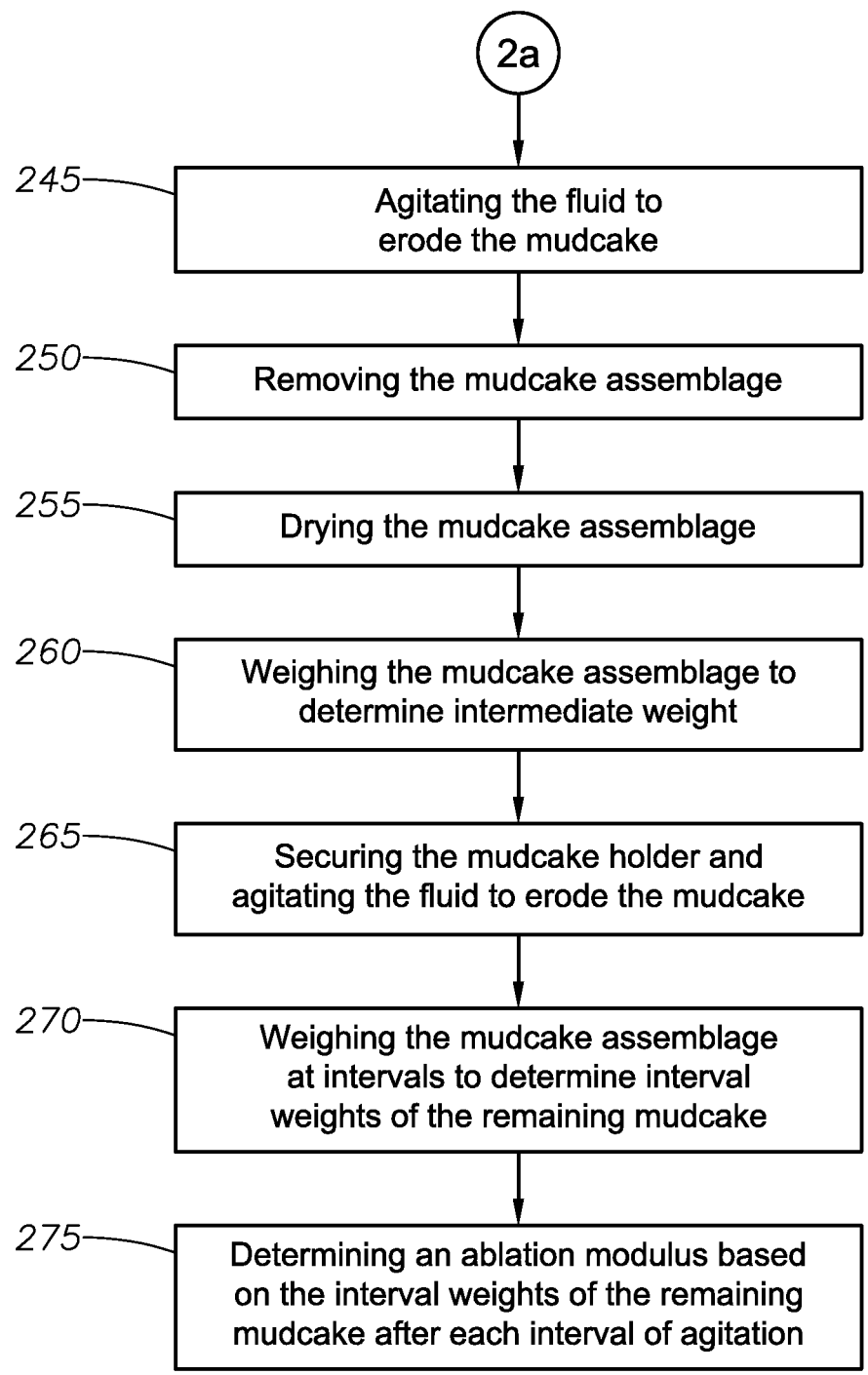

METHOD FOR ASSESSING ABLATION MODULAI OF MUDCAKES TO PREDICT EASE OF MUDCAKE REMOVAL OR CLEANING EFFICIENCY OF CLEANING/WASHING/SPACER FLUIDS

RELATED APPLICATION

This application is related to, and claims priority to, U.S. Provisional Patent Application Ser. No. 61/739,828, filed on Dec. 20, 2012, the disclosure of which is incorporated herein by reference in its entirety.

BACKGROUND

Field of the invention

Embodiments of the invention generally relate to methods for determining the erosional characteristics of a mudcake in the presence of a washing/cleaning/spacer fluid (hereinafter collectively referred to as a "cleaning fluid"). More specifically, various embodiments of the invention relate to methods for measuring the efficiency of a cleaning fluid for removing the mudcake from a wellbore wall prior to well completion. In particular, some embodiments of the invention relate to methods for determining the ease of removing the mudcake from a wellbore wall by hydrodynamic action in the presence of a native fluid. Other embodiments of the invention relate to methods for determining the ease of removing the mudcake by the combined action of hydrodynamic forces and chemical interactions generated by a foreign fluid on the mudcake. Additionally, some embodiments of the invention relate to methods for determining a minimum soaking or interaction time required for the cleaning fluid to maximize the amount of the mudcake removed from the borehole or wellbore wall (hereinafter collectively referred to as a "wellbore wall") prior to well completion.

Description of the Related Art

Horizontally/multilaterally-drilled wells have been used to enhance both hydrocarbon recovery and total well productivity from many types of reservoirs. Drilling, workover, and production operations may result in near-wellbore formation damage that in most cases cannot be prevented (e.g., pore plugging by calcium carbonate particles from drilling fluid, drilled solid particles, or particles from the formation).

During well operations, drilling fluids can be lost into the surrounding formation. To prevent this, the drilling fluid is frequently modified such that a small amount of the fluid and solids contained therein form a coating on a wellbore surface (i.e., the formation of a "filter cake" or "mudcake"—hereinafter referred to as a "mudcake"). After the completion of drilling operations, the mudcake is typically removed, and production from the formation can proceed. The process used to remove the mudcake can also be used to remove other types of damage or debris from the wellbore prior to beginning hydrocarbon production.

Effective removal of the mudcake prior to completing a well is very important for production of a well in commercial rate. Mudcake removal, though important for all wells, is very important for horizontal wells with barefoot completions. Failure of some horizontal wells to produce in commercial rates are related to plugging of the sand screens by the leftover mudcake materials and/or creation of a strong flow barrier at the cement-wellbore interface. The presence of some mudcake material on the wellbore wall dramatically reduces oil flow caused by the extremely low permeability of the mudcake. Typically, mudcake permeability ranges from 0.005 to 0.0012 mD (millidarcy). Hence, inadequate cleaning of the mudcake from the wellbore wall will create a highly detrimental effect on the productivity of a well.

Currently, there are no available, well-defined quantitative methods or API method for evaluating an ablation modulus of a mudcake in the presence of a native or foreign fluid. A reliable, well-defined, but simple, quantitative and statistically valid test facility and laboratory method, therefore, is needed for adequately evaluating the ablation modulus of a mudcake in the presence of a native or foreign fluid to determine the mudcake removal efficiency of various cleaning fluids.

SUMMARY OF THE INVENTION

The effective removal of mudcake from a wellbore wall is an important aspect of completing a well. For example, if the mudcake is not sufficiently removed or cleaned from the wellbore, then the remaining mudcake may cause a faulty primary cementation of the wellbore due to the absence of well-established bonding between the cement and the wellbore wall. The absence of bonding may create channeling in the cement-wellbore wall interface, thus preventing adequate support to maintain the integrity of the well. Hence, a secondary cementation of the wellbore may be required, significantly increasing well completion cost. The poor primary cementation of the wellbore may also lead to underground blowout due to inadequate support of the faulty cement sheath. In a worst case scenario, the underground blowout may cause a total loss of the well. For at least these reasons, the completion of a well requires an efficient cleaning of the mudcake from the wellbore wall prior to cementation of the wellbore.

For effective removal of mudcake from the wellbore wall, it is essential to create adequate hydrodynamic conditions to dislodge and remove the mudcake from the borehole wall. The mudcake may be removed from the wellbore wall by two primary fluid hydraulic threes: (1) hydrodynamic forces generated by the application of a native fluid on the mudcake, or (2) the combined action of hydrodynamic forces and chemical interactions generated by the application of a foreign fluid, for example, the cleaning fluid, on the mudcake. Adequate hydrodynamic conditions are generated to dislodge and remove the mudcake from the wellbore wall when the cleaning fluid provides a good mudcake-fluid interaction, thereby removing and transporting both the mudcake materials and the by-products generated by the chemical interaction there between.

Conventional laboratory processes have been developed to create simulated physical wellbore environments in an attempt to extract accurate experimental data for the relative performance and efficiency of various cleaning fluids for removing mudcakes from a wellbore prior to well completion. Conventional laboratory process, however, have been unable to provide an accurate and reliable comparison of cleaning fluids due to the presence of technical errors associated with sample positioning, mechanical stability of the set-up and test conditions, and human errors associated with placing, positioning, recovering, and measuring the mudcake before and after respective tests.

Various embodiments of the invention provide methods for measuring the efficiency of a cleaning fluid for removing mudcake from a wellbore wall prior to well completion. In particular, some embodiments of the invention relate to methods for determining the ease of removing the mudcake from a wellbore wall by hydrodynamic action in the presence of a native fluid. Other embodiments of the invention relate to methods for determining the ease of removing the mudcake by the combined action of hydrodynamic forces and chemical interactions generated by a foreign fluid on the mudcake. Additionally, some embodiments of the invention relate to methods for determining a minimum soaking or interaction time required for the cleaning fluid to maximize the amount of the mudcake removed from the wellbore wall prior to well completion.

Therefore, in accordance with an embodiment of the invention, there is provided a method for determining an ablation modulus of a mudcake on a wellbore wall. The method includes preparing a mudcake, forming a mudcake assemblage comprising the prepared mudcake, a screen, and a filter paper, and submerging and securing the mudcake assemblage in a container filled with a fluid. The fluid includes one of a native fluid or a foreign fluid to the mudcake. The method further includes agitating the fluid for a plurality of time intervals, removing the mudcake assemblage from the container after expiration of each time interval, and drying the mudcake assemblage. Further, the method includes weighing the mudcake assemblage to determine an interval weight for each time interval, and determining the ablation modulus of the mudcake on the wellbore wall by graphically correlating the determined interval weights of the remaining mudcake in the mudcake assemblage as a function of time. The ablation modulus of the mudcake is defined by a slope of a tangent of an initial portion of the graphical correlation between the determine interval weights and cumulative time.

In accordance with another embodiment, the step for preparing includes preparing the mudcake selected from the group consisting of a fresh water mudcake, a salt water mudcake, and a Saudi volcanic ash (SAVA)-based mudcake.

In accordance with another embodiment, the step for agitating includes agitating the fluid at a constant rate at about 15 minute time intervals.

In accordance with another embodiment, the method further includes soaking the mudcake assemblage in the fluid in the container before agitating the fluid for the plurality of time intervals.

In accordance with another embodiment, the mudcake assemblage is soaked in the fluid in the container for at least about 2 hours.

In accordance with another embodiment, the step for drying includes drying the mudcake assemblage for at least about 2 minutes before weighing the mudcake assemblage to determine the interval weight for each time interval.

In accordance with another embodiment, the native fluid includes fresh water for a fresh water-based mudcake, salt water for a salt water-based mudcake, and base oil for a SAVA-based mudcake.

In accordance with another embodiment, the foreign fluid includes one of a cleaning fluid, a washing fluid, and a spacer fluid, which is used for effective removal of the mudcake from the wellbore wall.

In accordance with another embodiment, the foreign fluid further includes one of an acid, an enzyme, and a chemical spacer used in-between the mudcake and the cement slurry.

In accordance with another embodiment of the invention, there is provided an apparatus for determining an ablation modulus of a mudcake on a wellbore wall. The apparatus includes a mudcake assemblage comprising the mudcake, a screen, and a filter paper, and a container filled with a fluid. The fluid includes one of a native fluid or a foreign fluid to the mudcake. The container is configured to hold the mudcake assemblage submerged in the fluid. The apparatus further includes an agitator configured to agitate the fluid for a plurality of time intervals, such that the agitated fluid applies a force to a surface of the mudcake to erode the mudcake. Further, the apparatus includes a processor configured to weigh the mudcake assemblage to determine an interval weight for each time interval. The processor is configured to determine the ablation modulus of the mudcake on the wellbore wall by graphically correlating the determined interval weights of the remaining mudcake in the mudcake assemblage as a function of time. The ablation modulus of the mudcake is defined by a slope of a tangent of an initial portion of the graphical correlation between the determine interval weights and cumulative time.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIGS. 2a and 2b are flow diagrams of a method for determining an ablation modulus of a mudcake on a wellbore wall, in accordance with an embodiment of the invention.

DETAILED DESCRIPTION OF THE INVENTION

Figure 1:
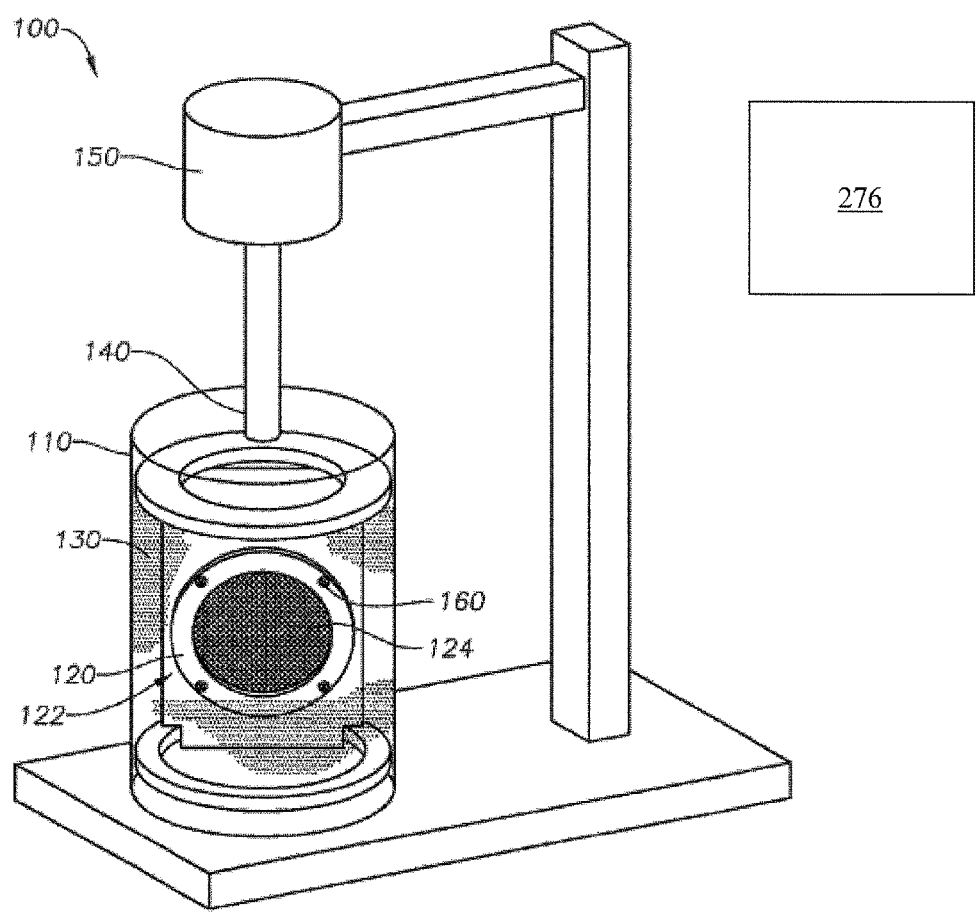
FIG. 1 is a schematic diagram of an apparatus, in accordance with an embodiment of the invention.

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout.

Various embodiments of the invention recognize that effective removal of mudcake from a wellbore wall requires adequate hydrodynamic conditions to dislodge and remove the mudcake from the wellbore wall by the action of hydrodynamic forces or the selection of a cleaning fluid that provides a good mudcake-fluid interaction to remove and transport the mudcake materials and the interaction by-products from the wellbore wall prior to cementation of the wellbore.

In particular, various embodiments provide a method for determining an initial ablation modulus ($A_{im}$) of a mudcake due to the hydrodynamic action on the mudcake in the wellbore by a native fluid or due to the combined action of hydrodynamic forces and chemical interactions between the mudcake and a reactive foreign fluid in the wellbore. According to at least one embodiment, the native fluids that are used to create hydrodynamic action on the mudcake include, for example, fresh water for fresh water-based mudcakes, salt water for salt water-based mudcakes, and base oil for SAVA-based mudcakes. The foreign fluids that are used to create chemical interactions with the mudcake, in addition to the hydrodynamic effect on the mudcake, include, for example, different cleaning fluids used for effective removal of mudcake from the wellbore wall. According to various embodiments, the foreign fluids are cleaning fluids containing, for example, acids and/or enzymes, chemical spacers used in-between the mudcake and the cement slurry, etc. In the presence of a foreign fluid, mild to severe interaction occurs between the mudcake and foreign fluid depending on the chemical strength of the foreign fluid and the interaction capability with a particular mudcake, in addition to the hydrodynamic action, the foreign fluid interacts with the mudcake matrix to destroy inter-particle bonds and/or dissolve matrix material for easy removal of the mudcake from the wellbore wall. Accordingly, the foreign fluid performs two actions during the mudcake cleaning process.

According to at least one embodiment of the invention, the ablation modulus resulting from the hydrodynamic action on the mudcake in the wellbore by the native fluid is designated as $A_{imh}$ to indicate an initial ablation modulus due to hydrodynamic action only. In the presence of a native fluid, no interaction occurs between the mudcake and the native fluid due to the compatibility of the two materials. The main function of the native fluid is to transmit the hydrodynamic tearing, shearing, and eroding action on the mudcake material to remove it from the wellbore wall and transport the mudcake out of the wellbore with the native fluid.

On the other hand, the ablation modulus resulting from the combination of hydrodynamic action and the chemical interaction between the mudcake and the foreign fluid is designated as $A_{imhi}$ to indicate an initial ablation modulus due to the combined effect of hydrodynamic and chemical actions.

As will be discussed in more detail below, embodiments of the invention directed to the hydrodynamic action on the mudcake material on the wellbore wall by native fluids are created by mechanical agitation of a native fluid by rotating, for example, a laboratory agitator at a constant speed, for example, at least about 2500 revolutions per minute (rpm), to simulate the hydrodynamic conditions of the wellbore in a test cell and the well cleaning process that occurs prior to cementation of the wellbore in the absence of a foreign fluid. As previously noted, the ablation modulus due to hydrodynamic action is designated as $A_{imh}$. According to various embodiments, the process is conducted in the presence of a foreign fluid, for example, the cleaning fluid. As previously noted, the ablation modulus due to the combined effect of hydrodynamic and chemical actions is designated as $A_{imhi}$.

According to various embodiments, all mudcakes have some loose gel-like mud materials at the top of the mudcake that is not the part of the mudcake, and thus should be excluded from the determination of the mudcake mass loss. To exclude the effect of the loose gel-like material, the mudcake is initially washed, for example, for 2 minutes at a constant speed, for example, 1000 rpm, to remove the loose gel-like material from the mudcake top. Hence, in accordance with various embodiments, the loose gel-like material at the top of the mudcake has no effect on the test results, and thus provides reliable indication of the removal efficiency of the mudcake.

As will be discussed in more detail below, several tests were conducted using two fresh water and one salt water-based mudcakes to demonstrate the application of various methods for evaluating the ablation modulus of a mudcake in the presence of a native or foreign fluid to determine the mudcake removal efficiency of various cleaning fluids. Data collected from these tests were used to plot remaining mass of the mudcake on the wellbore wall versus cumulative time curves. According to various embodiments, the slope of the initial linear portion of the plotted curves is used to determine the initial rate of loss of mudcake material on agitation defined by an index parameter, i.e., the ablation modulus of the mudcake. As will be discussed below, the results of this collected data, as illustrated in the plotted curves, demonstrate the suitability of the mudcake removal methods, according to various embodiments, for mudcake removal efficiency evaluation of various fluids, including both native and foreign fluids, prior to cementation of the wellbore or well completion.

FIG. 1 is a schematic diagram of an apparatus, in accordance with an embodiment of the invention. In accordance with various embodiments, as shown in FIG. 1, the apparatus 100 includes a cell 110, for example, an erosion cell having a size, for example, of at least 1500 cc, to represent a section of a wellbore. The apparatus 100 further includes a mudcake holder 120 that securely holds a mudcake thereto. The mudcake holder 120 is sized to fit within the cell 110. In accordance with at least one embodiment, the mudcake holder 120 is sized to fit tightly within the cell 110 to prevent any motion of the holder during agitation of a cleaning fluid 130 in the cell 110. According to at least one embodiment, the mudcake holder 120 includes a mudcake assemblage 122 having a metal screen 124 and filter paper (not shown).

In accordance with various embodiments, the apparatus 100 further includes a variable speed agitator system including, for example, a fluid agitator 140 and a variable speed motor 150 that simulates a scaled-down effect of dynamic annular flow of a wellbore.

According to at least one embodiment, the apparatus 100 further includes one or more securing screws 160 to secure the mudcake assemblage 122 into a circular recess of the mudcake holder 120 to prevent any motion of the mudcake assemblage 122 during agitation of the cleaning fluid 130 in the cell 110. The prevention of the motion of the mudcake assemblage 122 while testing eliminates, or at least minimizes, experimental error.

In accordance with at least one embodiment, the apparatus 100 is operatively connected an electronic measuring device (not shown), for example, a high precision electronic measuring scale to measure the weight of the mudcake before and after respective tests.

As shown in FIG. 1, the fixation of a mudcake assemblage firmly in a mudcake holder eliminates measurement error associated with mudcake movement while testing. The central position of an agitator spindle and its location at the same depth for all mudcakes ensure similar hydrodynamic conditions for all tests, and thus eliminate, or at least minimize, experimental error. The easy removal of the mudcake from the cell by removing the mudcake holder from the test cell eliminates the loss of materials associated with removal of mudcake from the test cell, and thus eliminates, or at least minimizes, human error.

Figure 2A:
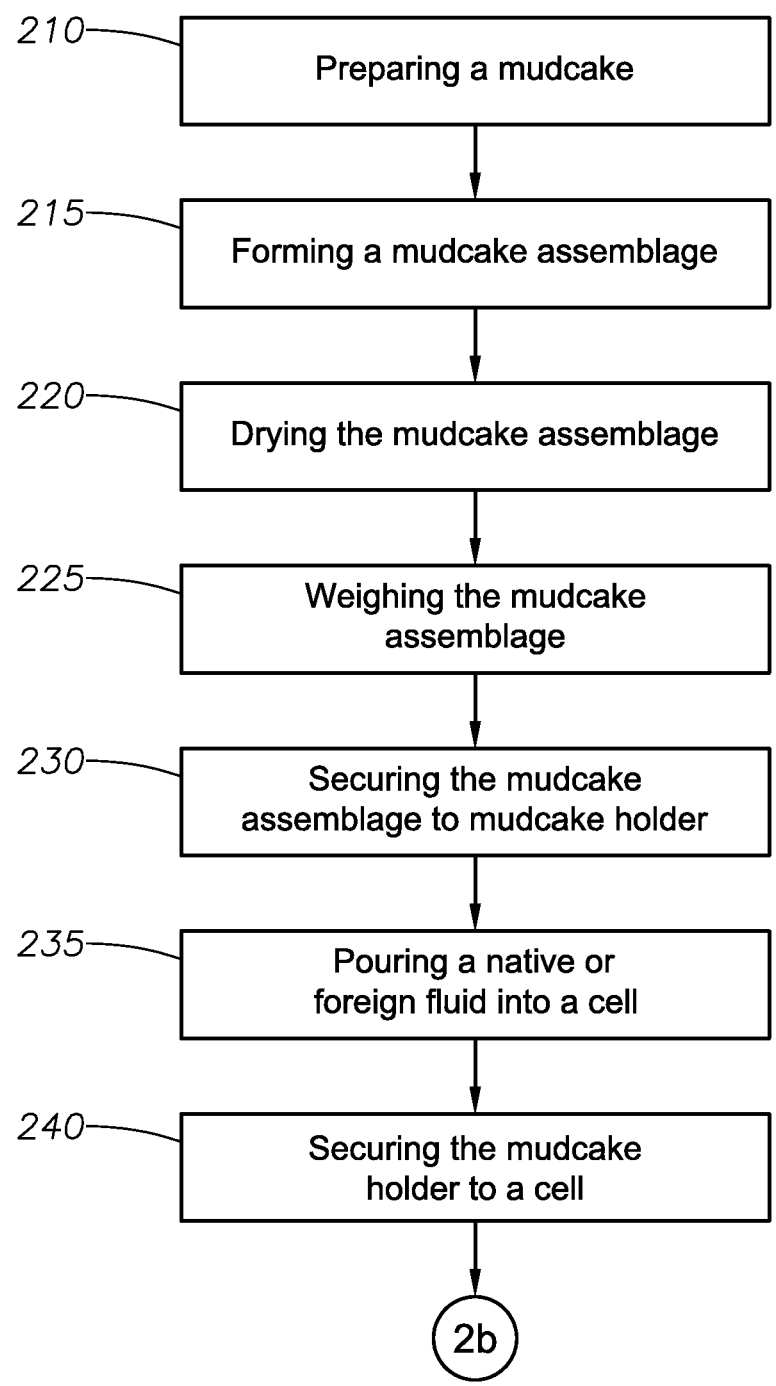

FIGS. 2a and 2b are flow diagrams of a method for determining an ablation modulus of a mudcake on a wellbore wall, in accordance with an embodiment of the invention. As shown in FIG. 2a, the method includes preparing, at step 210, a mudcake, for example, using an API or high temperature, high pressure filtration apparatus, and forming, at step 215, a mudcake assemblage comprising the prepared mudcake, a screen, and filter paper. The screen includes, for example, a metal screen. The method further includes drying, at step 220, the mudcake assemblage for a predetermined period of time, for example, at least 2 minutes. The method further includes weighing, at step 225, the mudcake assemblage to determine an initial weight of the mudcake assemblage.

Further, as shown in FIG. 2a, the method includes securing, at step 230, the mudcake assemblage to a mudcake holder, and pouring, at step 235, an amount of a fluid into the cell, the fluid including one of a native fluid and a foreign fluid. In accordance with at least one embodiment, the native fluid includes a fluid that is compatible with a matrix of the mudcake. The native fluid includes, for example, fresh water for a fresh water mudcake, salt water for a salt water mudcake, or base oil for a SAVA-based mudcake. When the native fluid flows across the surface of the mudcake a hydrodynamic force is applied to the mudcake. In accordance with at least one other embodiment, the foreign fluid creates a chemical interaction with the mudcake, in addition to the hydrodynamic force applied to the mudcake. The foreign fluid includes, for example, one of a cleaning fluid, a washing fluid, and a spacer fluid, which is used for effective removal of mudcake from the wellbore wall. According to various embodiments, the foreign fluid is a cleaning fluid containing, for example, acids and/or enzymes and chemical spacers used in-between the mudcake and the cement slurry. In the presence of a foreign fluid, mild to severe interaction occurs between the mudcake and foreign fluid depending on the chemical strength of the foreign fluid and the interaction capability with a particular mudcake. In addition to the hydrodynamic action, the foreign fluid interacts with the mudcake matrix to destroy inter-particle bonds and/or dissolve matrix material for easy removal of the mudcake from the wellbore wall. Accordingly, the foreign fluid performs two actions during the mudcake cleaning process.

The method further includes securing, at step 240, the mudcake holder into the cell such that the mudcake holder are submerged below the surface of the fluid in the cell. Accordingly, in accordance with at least one embodiment, the amount of the fluid in the cell is about 1500 mL of the fluid. The step of placing the mudcake holder into the cell includes securing the mudcake holder to the cell to maintain the mudcake holder in a stationary position during agitation of the fluid.

As shown in FIG. 2b, the method further includes agitating, at step 245, the fluid, using an agitator, to erode the mudcake, whereby the agitator is centrally positioned within the cell. In accordance with some embodiments of the invention, the fluid is agitated for a predetermined time, for example, for about 5 minutes at a constant speed, for example, about 1000 revolutions per minute to remove all loose gel-like materials from the top surface of the mudcake.

In accordance with another embodiment of the invention, the effective interaction time of the fluid can be evaluated by agitating, at step 245, the fluid after the mudcake has been allowed to soak in the fluid for an interval of time, for example, about 2, 4, 6, 8, etc, hours.

Further, as shown in FIG. 2b, the method includes removing, at step 250, the mudcake holder from the cell and the mudcake assemblage from the mudcake holder, and drying, at step 255, the mudcake assemblage for a predetermined period of time, for example, at least 2 minutes. The method further includes weighing, at step 260, the mudcake assemblage to determine an intermediate weight of the mudcake assemblage, after removal of the gel-like materials from the top surface of the mudcake.

The method further includes placing the mudcake holder back into the cell and agitating, at step 265, the fluid, for an interval of time, for example, 15, 30, 45 cumulative minutes, whereby the mudcake holder is removed after each 15 minute intervals, so that the mudcake assemblage can be weighed, at step 270, after a drying period, each measurement defining an interval weight of the mudcake assemblage.

The method further includes determining, at step 275, using a processor 276, an ablation modulus of the mudcake based on the interval weights of the remaining mudcake after each interval of agitation. In accordance with various embodiments, the ablation modulus of the mudcake is defined by the slope of a tangent of an initial linear portion of an interval weight versus cumulative time curve for the mudcake.

In the presence of a native fluid in the cell, the ablation modulus indicates the ease of removal of the mudcake under the action of a hydrodynamic action of the fluid flow. In the presence of a foreign fluid, the ablation modulus indicates the cleaning efficiency of a foreign fluid under the combined action of hydrodynamic and chemical interaction forces. Hence, in accordance with various embodiments, the method, as shown in FIGS. 2a and 2b, is equally applicable for a relative ranking of erosional resistance of various mudcakes under a native fluid or the relative ranking of different cleaning fluids for a particular mudcake composition.

Experimentation was conducted using the apparatus shown in FIG. 1, using the method described in FIGS. 2a and 2b, to evaluate the ease of removal of several mudcakes in the presence of their respective native fluids, i.e. fresh water for a fresh water bentonite mudcake, salt water for a salt water bentonite mudcake, and fresh water for a fresh water-based SAVA mudcake.

Table 1 shows experimental data showing agitation time versus mudcake weight.

TABLE 1

| Agitation Time (minutes) | Bentonite Mudcake Weight (gm) | Salt Water Bentonite Mudcake Weight (gm) | SAVA Mudcake Weight (gm) |
| --- | --- | --- | --- |
| 0 | 8.258 | 21.658 | 8.758 |
| 15 | 4.582 | 10.622 | 6.522 |
| 30 | 1.813 | 8.813 | 4.713 |
| 45 | 0.373 | 6.813 | 4.013 |

Table 2 shows the composition of the fresh water bentonite mudcake and the associated mudcake test results.

TABLE 2

| | |
| --- | --- |
| Water (ml) | 350 |
| Bentonite (gm) | 20 |

TABLE 2-continued

| NaOH (gm) | As required to raise pH to 9.5-10 |
|---|---|

| Time (min) | Filter Paper + Mudcake Weight (gm) | Mudcake Weight (gm) |
|---|---|---|
| 0 | 9.4 | 8.258 |
| 15 | 5.76 | 4.582 |
| 30 | 3 | 1.813 |
| 45 | 1.56 | 0.373 |

Table 3 shows the composition of the salt water bentonite mudcake and the associated mudcake test results.

TABLE 3

| Water (ml) | 350 |
|---|---|
| Bentonite (gm) | 20 |
| NaCl (gm) | 25 |
| NaOH (gm) | As required to raise pH to 9.5-10 |

| Time (min) | Filter Paper + Mudcake Weight (gm) | Mudcake Weight (gm) |
|---|---|---|
| 0 | 22.8 | 21.658 |
| 15 | 11.8 | 10.622 |
| 30 | 10 | 8.813 |
| 45 | 8 | 6.813 |

Table 4 shows the composition of the SAVA mudcake and the associated mudcake test results.

TABLE 4

| Water (ml) | 350 |
|---|---|
| SAVA (gm) | 20 |
| XC Polymer (gm) | 2 |
| PHP (gm) | 2 |
| NaOH (gm) | As required to raise pH to 9.5-10 |

| Time (min) | Filter Paper + Mudcake Weight (gm) | Mudcake Weight (gm) |
|---|---|---|
| 0 | 9.9 | 8.758 |
| 15 | 7.7 | 6.522 |
| 30 | 5.9 | 4.713 |
| 45 | 5.2 | 4.013 |

Figure 3A:
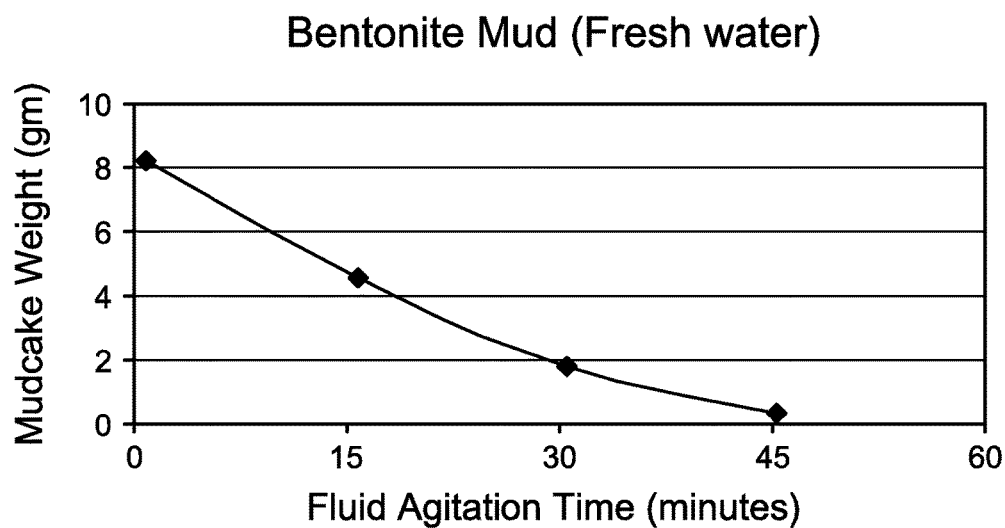
FIG. 3a is a graph showing a relationship between the remaining mass of a fresh water bentonite mudcake on a wellbore wall versus cumulative time, in accordance with an embodiment of the invention.
Figure 3B:
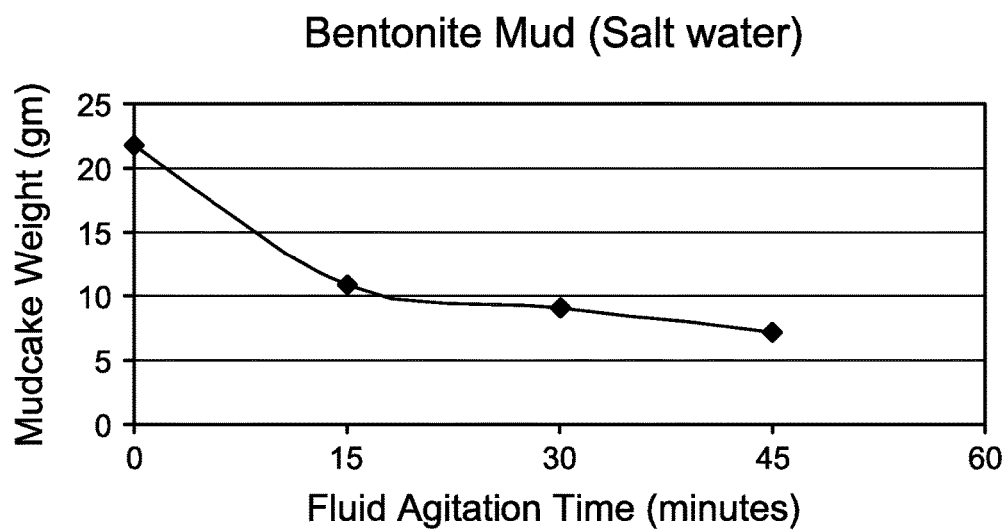
FIG. 3b is a graph showing a relationship between the remaining mass of a salt water bentonite mudcake on a wellbore wall versus cumulative time, in accordance with an embodiment of the invention.
Figure 3C:
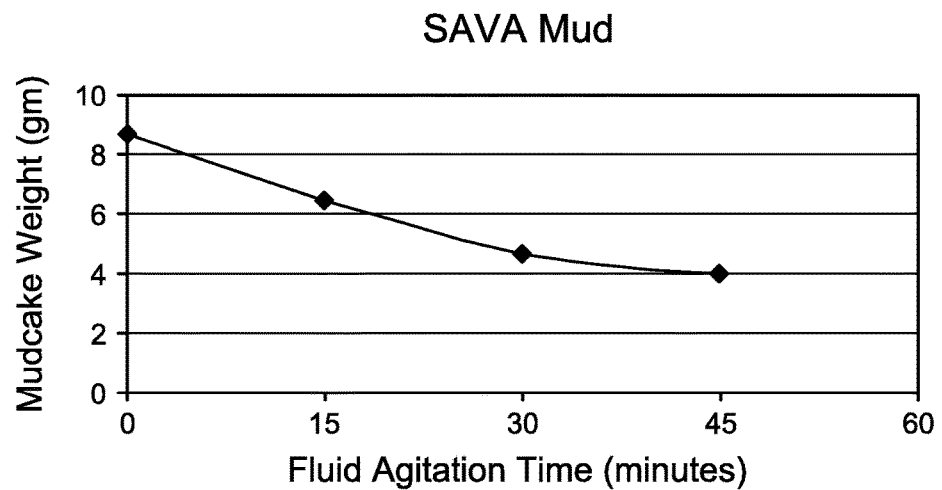
FIG. 3c is a graph showing a relationship between the remaining mass of a SAVA mudcake on a wellbore wall versus cumulative time, in accordance with an embodiment of the invention.

FIGS. 3a, 3b, and 3c are graphs showing a relationship between the remaining mass of different mudcakes on the wellbore wall versus cumulative time, in accordance with an embodiment of the invention. In particular, FIG. 3a is a graph showing a relationship between the remaining mass of a fresh water bentonite mudcake on a wellbore wall versus cumulative time, in accordance with an embodiment of the invention. FIG. 3b is a graph showing a relationship between the remaining mass of a salt water bentonite mudcake on a wellbore wall versus cumulative time, in accordance with an embodiment of the invention. FIG. 3c is a graph showing a relationship between the remaining mass of a SAVA mudcake on a wellbore wall versus cumulative time, in accordance with an embodiment of the invention.

Figure 4:
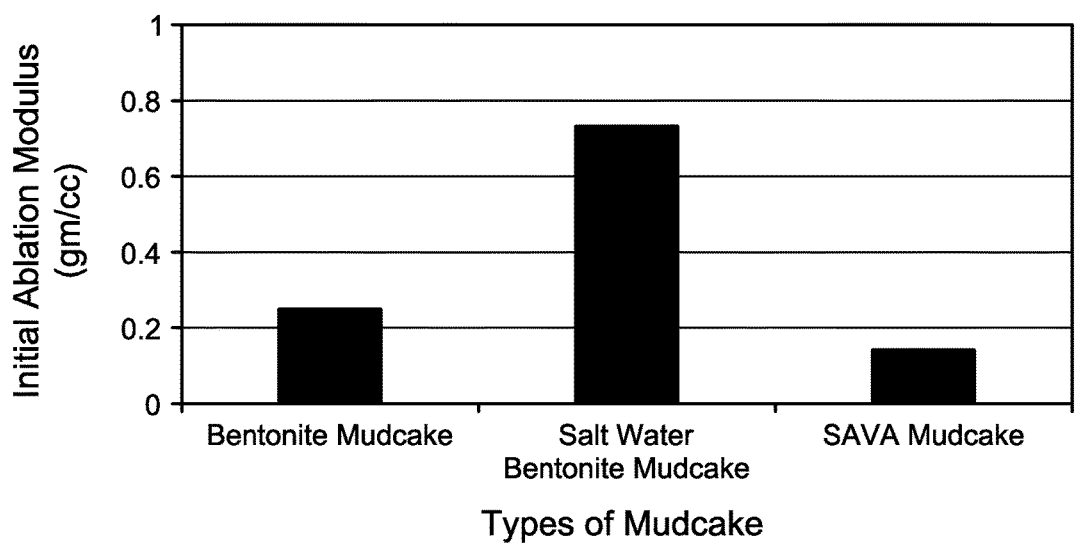
FIG. 4 shows the ablation moduli of the three different mudcakes tested using the methods described above for FIGS. 2a and 2b, according to various embodiments of the invention.

The initial rate of loss of the mudcake material, i.e., the ablation moduli of the mudcakes, was determined as the slope of each of the initial part of the remaining mass versus cumulative time curves. FIG. 4 shows the ablation moduli of the three different mudcakes tested using the methods described above for FIGS. 2a and 2b, according to various embodiments of the invention.

As shown in FIG. 4, according to the experimental data for various embodiments of the invention, a weakly bonded salt water bentonite mudcake has the highest initial loss of mudcake material on agitation, and thus provides the highest initial ablation modulus. According to other embodiments, a well bonded SAVA mudcake has the lowest initial loss of mudcake material on agitation, and thus provides the lowest initial ablation modulus. Experimental data shows that a bentonite mudcake has intermediate initial loss of mudcake material on agitation, and thus provides an intermediate value of the initial ablation modulus.

The ablation moduli of mudcake, as shown in FIG. 4, indicate that the highest initial loss-on erosion is for the salt water bentonite mudcake acted upon by hydrodynamic action of the native fluid flow (salt water). The experimental results for various embodiments of the invention, demonstrate that the poor strength of the inter-particle bonds of the mudcake matrix lead to easy breakage of the bonds due to the destructive action of hydrodynamic forces. Hence, the salt water bentonite mud showed the highest rate of mudcake material erosion due to turbulence of the native fluid used for the test. It indicates that this type of mudcake can easily be cleaned from the wellbore walk even by creating appropriate hydrodynamic conditions using a native fluid as the cleaning medium.

Experimentation for the fresh water bentonite mudcake shows an intermediate value of ablation modulus which is nearly three times lower than the ablation modulus of the salt water bentonite mud. The fresh water bentonite mudcake, however, has a higher ablation modulus than the SAVA mudcake used to validate the various methods according to embodiments of the invention. The SAVA mudcake showed the lowest ablation modulus which is reflected by the lowest amount of initial loss of mudcake material during the test. This mudcake will require stronger hydrodynamic forces for adequate cleaning of the mudcake from the wellbore wall or a combination of hydrodynamic force and chemical interaction using a foreign fluid for adequate cleaning of the mudcake from the wellbore wall. In case of a mudcake with a low ablation modulus under the action of hydrodynamic forces, the cleaning or removal of the mudcake from the wellbore wall can be improved by treating the mudcake with a suitable cleaning fluid before completing a well. In that case, the ablation modulus will reflect the combined action of the hydrodynamic and chemical debonding forces, i.e., hydro-chemical effect of the mudcake cleaning process. Hence, the methods, according to various embodiments of the invention, are equally applicable in evaluating the mudcake removal efficiency of different cleaning fluid systems, and thus plays an important role in testing and evaluating different cleaning fluid systems to select the best cleaning fluid for efficient removal of a mudcake from a wellbore wall prior to a cementation or well completion of a well.

Embodiments of the invention provide non-obvious advantages over conventional laboratory processes. For example, various embodiments provide methods for selecting the most suitable cleaning fluid system that is compatible to the chemistry of a deposited mudcake material to ensure effective removal of the mudcake from a wellbore wall before a completion of the well. The operational benefits of the proper removal of the mudcake from the wellbore wall include, for example, assurance of a good cementation of the well, removal of the mudcake associated formation damage, and improvement of oil productivity. The assurance of a good primary cementation of the well also eliminates the need for any secondary cementation of the well, and thus significantly reduces the well completion cost. The elimination of formation and screen damage associated with mudcake materials also improves well productivity and enhances the return on investment of the well.

The present invention may suitably comprise, consist or consist essentially of the elements disclosed and may be practiced in the absence of an element not disclosed. For example, it can be recognized by those skilled in the art that certain steps can be combined into a single step.

Unless defined otherwise, all technical and scientific terms used have the same meaning as commonly understood by one of ordinary skill in the art to which this invention belongs.

The singular forms "a," "an," and "the" include plural referents, unless the context clearly dictates otherwise.

As used herein and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

What is claimed is:

1. A method for determining an ablation modulus of a mudcake on a wellbore wall, the method comprising:
    preparing a mudcake;
    forming a mudcake assemblage comprising the prepared mudcake and a screen;
    submerging and securing the mudcake assemblage in a container filled with a fluid, the fluid comprising one of a native fluid or a foreign fluid to the mudcake;
    washing the mudcake for a time period of at least 2 minutes at a first speed, such that loose gel-like mud materials are removed from a top of the mudcake;
    agitating the fluid at a second speed greater than the first speed for a plurality of time intervals after washing the mudcake, wherein the second speed is at least 2500 rpm;
    removing the mudcake assemblage from the container after expiration of each time interval;
    drying the mudcake assemblage;
    weighing the mudcake assemblage to determine an interval weight for each time interval; and
    determining the ablation modulus of the mudcake on the wellbore wall by graphically correlating the determined interval weights of the remaining mudcake in the mudcake assemblage as a function of time, wherein the ablation modulus of the mudcake is defined by a slope of a tangent of an initial portion of the graphical correlation between the determine interval weights and cumulative time, the initial portion corresponding to a portion between a zero agitation time and a first time interval of the plurality of time intervals.

2. The method of claim 1, wherein the preparing comprises preparing the mudcake selected from the group consisting of a fresh water mudcake, a salt water mudcake, and a Saudi volcanic ash (SAVA)-based mudcake.

3. The method of claim 1, wherein the agitating comprises agitating the fluid at a constant rate at 15 minute time intervals.

4. The method of claim 1, wherein the drying comprises drying the mudcake assemblage for at least 2 minutes before weighing the mudcake assemblage to determine the interval weight for each time interval.

5. The method of claim 1, wherein the native fluid comprises fresh water for a fresh water-based mudcake, salt water for a salt water-based mudcake, and base oil for a Saudi volcanic ash (SAVA)-based mudcake.

6. The method of claim 1, further comprising:
    soaking the mudcake assemblage in the fluid in the container before agitating the fluid for the plurality of time intervals.

7. The method of claim 6, wherein the mudcake assemblage is soaked in the fluid in the container for at least 2 hours.

8. The method of claim 1, wherein the foreign fluid comprises one of a cleaning fluid, a washing fluid, and a spacer fluid, which is used for effective removal of the mudcake from the wellbore wall.

9. The method of claim 8, wherein the foreign fluid further comprises one of an acid and an enzyme.

10. An apparatus for determining an ablation modulus of a mudcake on a wellbore wall, the apparatus comprising:
    a mudcake assemblage comprising the mudcake and a screen;
    a container filled with a fluid, the fluid comprising one of a native fluid or a foreign fluid to the mudcake, the container being configured to hold the mudcake assemblage submerged in the fluid;
    an agitator configured to agitate the fluid at a speed of at least 2500 revolutions per minute (rpm) for a plurality of time intervals, such that the agitated fluid applies a force to a surface of the mudcake to erode the mudcake; and
    a processor configured to weigh the mudcake assemblage to determine an interval weight for each time interval, the processor being configured to determine the ablation modulus of the mudcake on the wellbore wall by graphically correlating the determined interval weights of the remaining mudcake in the mudcake assemblage as a function of time, wherein the ablation modulus of the mudcake is defined by a slope of a tangent of an initial portion of the graphical correlation between the determine interval weights and cumulative time, the initial portion corresponding to a portion between a zero agitation time and a first time interval of the plurality of time intervals.

11. The apparatus of claim 10, wherein the mudcake is selected from the group consisting of a fresh water mudcake, a salt water mudcake, and a Saudi volcanic ash (SAVA)-based mudcake.

12. The apparatus of claim 10, wherein the agitator is configured to agitate the fluid at a constant rate at 15 minute time intervals.

13. The apparatus of claim 10, wherein the agitator is configured to agitate the fluid after the mudcake assemblage has been soaked for at least 2 hours.

14. The apparatus of claim 10, wherein the processor is configured to weigh the mudcake assemblage, after the mudcake assemblage has dried for at least about 2 minutes, to determine an interval weight for each time interval.

15. The apparatus of claim 10, wherein the native fluid comprises fresh water for a fresh water-based mudcake, salt water for a salt water-based mudcake, and base oil for a Saudi volcanic ash (SAVA)-based mudcake.

16. The apparatus of claim 10, wherein the foreign fluid comprises one of a cleaning fluid, a washing fluid, and a spacer fluid, which is used for effective removal of the mudcake from the wellbore wall.

17. The apparatus of claim 16, wherein the foreign fluid further comprises one of an acid and an enzyme.

\* \* \* \* \*